United States Patent [19]

Sumner, Jr.

[11] Patent Number: 5,041,616
[45] Date of Patent: Aug. 20, 1991

[54] PREPARATION OF ARYL KETONES

[75] Inventor: Charles E. Sumner, Jr., Kingsport, Tenn.

[73] Assignee: Eastman Kodak Company, Rochester, N.Y.

[21] Appl. No.: 574,023

[22] Filed: Aug. 29, 1990

[51] Int. Cl.$^5$ .................. C07C 67/08; C07C 67/29; C07C 45/00
[52] U.S. Cl. .................................. 560/144; 568/309; 568/319; 568/329; 568/332; 568/333
[58] Field of Search ............... 568/309, 319, 329, 332, 568/333; 560/144

[56] References Cited

FOREIGN PATENT DOCUMENTS 0075390 3/1983 European Pat. Off. .
0241306 10/1987 European Pat. Off. .

OTHER PUBLICATIONS

Rearson et al, Synthesis, (1972), pp. 533-542.

Primary Examiner—Jose G. Dees
Assistant Examiner—Vera C. Clark
Attorney, Agent, or Firm—J. Frederick Thomsen; William P. Heath, Jr.

[57] ABSTRACT

Disclosed is a process for the preparation of alkyl aryl ketones, cycloalkyl aryl ketones and diaryl ketones by contacting an aromatic compound with an aliphatic, cycloaliphatic or aromatic carboxylic acid in the presence of a catalytic amount of an organic sulfonic acid while removing the water of reaction as an azeotrope from the reaction mixture.

5 Claims, No Drawings

PREPARATION OF ARYL KETONES

This invention pertains to a process for the preparation of alkyl aryl ketones, cycloalkyl aryl ketones and diaryl ketones by contacting an aromatic compound with an aliphatic, cycloaliphatic or aromatic carboxylic acid. More particularly, this invention pertains to the preparation of aryl ketones by contacting an aromatic compound with a carboxylic acid in the presence of a catalytic amount of an organic sulfonic acid while removing the water of reaction as an azeotrope from the reaction mixture.

Aryl ketones are commercially useful as polymer intermediates, as precursors to polymer intermediates, in the preparations of dyestuffs and as antioxidants. One of the most common methods used to prepare aryl ketone involves the condensation of a carboxylic acid derivative with an active aromatic compound. Carboxylic acids are preferred starting materials because they are less expensive and less corrosive than the corresponding acid chlorides.

Aryl ketones typically are prepared by the reaction of an aromatic compound with an aromatic carboxylic acid chloride in the presence of a Friedel-Crafts catalyst such as aluminum chloride. Pearson et al describe in Synthesis, 1972, 533, the synthesis of diaryl ketones by heating an aromatic carboxylic acid chloride and an aromatic compound in the presence of a catalytic amount of a Lewis acid such as zinc chloride. The hydrochloric acid formed is removed and treated in its gaseous state.

British Patent 1,164,046 describes the preparation of aryl ketones by aromatic acylation using a carboxylic acid and liquid hydrogen fluoride as the condensing agent. The use of liquid hydrogen fluoride presents severe toxicity and corrosion problems. European Patent Application 87-303,162 describes the preparation of diaryl ketones (benzophenones) by contacting an aromatic compound with an aromatic carboxylic acid or an acid chloride thereof in the presence of a very strong acid such as trifluoromethanesulfonic acid and a weak acid (equal to chloroacetic acid) as solvent. A disadvantage to this method is that the solvent cannot be reused without drying it. European Patent Application 82-304,341 similarly discloses the reaction of an aromatic carboxylic acid with an aromatic compound in the presence of a stoichiometric amount of a fluoroalkanesulfonic acid to obtain diaryl ketones.

I have discovered that aryl ketones may be obtained by heating a carboxylic acid with certain aromatic compounds in the presence of (1) a volatile, organic compound which forms an azeotrope, i.e., a constant boiling mixture, with water and (2) a catalytic amount of an organic sulfonic acid, whereby the water of reaction is removed as an azeotrope from the reaction mixture. Advantages provided by my novel process include the use of a carboxylic acid rather than a carboxylic acid chloride which offers economic benefits and also eliminates the need to treat toxic byproducts. The use of catalytic, rather than stoichiometric, amount of the sulfonic acid catalyst is another advantage afforded by the present invention.

The process of my invention provides a means for the preparation of aryl ketones having the general formula

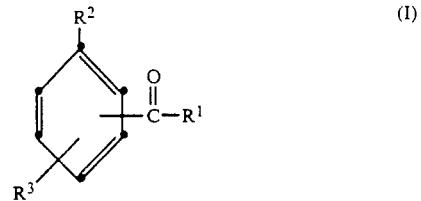

by heating a mixture of an aromatic compound having the general formula

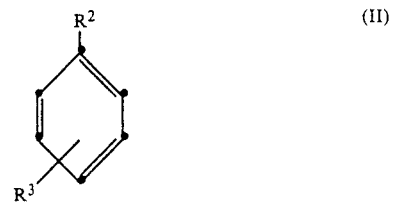

with a carboxylic acid in the presence of (1) a volatile, organic compound which forms an azeotrope with water and (2) a catalytic amount of an organic, sulfonic acid, whereby the water of reaction is removed as an azeotrope from the reaction mixture; wherein $R^1$ is the residue of a carboxylic acid;

$R^2$ individually is an alkyl, hydroxy, alkoxy, alkanoyloxy or aryl, e.g., phenyl, radical; and $R^3$ individually is hydrogen or one of the substituents which $R^2$ may represent; and $R^2$ and $R^3$ collectively represent a divalent chain of atoms forming a fused ring with the benzene ring to which each is attached, e.g., the radical —CH=CHCH=CH—. The residue collectively represented by $R^2$ and $R^3$ may be unsubstituted or substituted, for example, with one or two of the substituents which $R^2$ may represent.

The alkyl radical and the alkyl moiety of the alkoxy and alkanoyloxy which $R^2$ and/or $R^3$ can represent may contain up to about 20 carbon atoms and may be straight or branched chain, unsubstituted or substituted. $R^2$ and/or $R^3$ preferably represent lower ($C_1$-$C_4$) alkyl, e.g., methyl, hydroxy, lower alkoxy, e.g., methoxy, or lower alkanoyloxy, e.g., acetoxy.

The carboxylic acid employed is not critical and may be selected from a wide variety of unsubstituted and substituted, aliphatic, cycloaliphatic and aromatic carboxylic acids containing from 2 to 20 carbon atoms. Typical carboxylic acid reactants are included in the general formula

wherein $R^4$ is unsubstituted or substituted alkyl of up to about 19 carbon atoms, cyclohexyl, or phenyl or phenyl substituted with alkyl, alkoxy or alkylthio. $R^4$ preferably is alkyl of up to about 10 carbon atoms, phenyl or phenyl substituted with alkyl or alkoxy.

The organic, sulfonic acid may be selected from aliphatic, cycloaliphatic and aromatic sulfonic acids as well as polymer-bound sulfonic acid groups, e.g., polymers of sulfo-substituted styrene and/or divinylbenzene. Generally, the particular sulfonic acid catalyst that may be employed depends on the reactivity of the aromatic compound. For example, when the aromatic reactant is substituted with one or two activating (electron donating) groups such as hydroxy, alkoxy and/or alkanoyloxy, the acylation reaction is catalyzed by any organic, sulfonic acid. Thus, phenols and benzenediols, as well as ethers and esters thereof, may be acylated using methanesulfonic and toluenesulfonic acids. In the case of less reactive aromatic compounds such as alkylaromatic compounds, e.g., toluene and xylene, a more acidic sulfonic acid such as a perhaloalkylsulfonic acid, e.g., trifluoromethanesulfonic acid normally is required to achieve satisfactory reaction rates.

The amount of sulfonic acid catalyst employed can vary depending, for example, on the particular sulfonic acid employed, the reaction time and/or the aromatic compound reactant to be acylated. The catalytic amount of sulfonic acid typically is in the range of about 0.1 to 1.0 sulfo equivalents, preferably 0.3 to 1.0 sulfo equivalents per mole of carboxylic acid reactant. For the strongly acidic perhaloalkylsulfonic acids, e.g., trifluoromethanesulfonic acid, catalytic amount are in the range of about 5 to 50 mole percent based on the moles of carboxylic acid reactant.

My novel process is carried out in the presence of a volatile, organic compound which forms an azeotrope with water to permit the water by-product of the acylation reaction to be removed from the reaction mixture. The volatile, organic compound selected should form a water azeotrope having a boiling point of at least 65° C., typically from about 90° to 100° C., at atmospheric pressure. Examples of suitable azeotrope-forming compounds include aromatic hydrocarbons such as toluene, xylene, mesitylene, cumene and ethylbenzene; and aliphatic hydrocarbons such as heptane, nonane, octane and decane. The azeotrope-forming compound and the aromatic compound reactant may be the same, e.g., in the acylation of toluene and p-xylene. When the aromatic reactant is not an azeotrope-forming, volatile compound, an azeotrope-forming compound is used in an amount which is sufficient to remove all of the water of reaction, e.g., at least one mole of volatile, organic compound per mole of carboxylic acid. Normally, however, the volatile, organic compound is employed in a substantial excess and may function as the process solvent as well as the azeotroping compound.

My process may be performed at a temperature in the range of about 80° to 200° C., depending on the particular reactants and/or azeotroping agent employed. Preferred reaction temperatures are in the range of about 110° to 165° C.

A preferred embodiment of the present invention concerns the preparation of dialkyl benzophenones, particularly dimethyl benzophenone, by the reaction of an aromatic acid such as benzoic acid with xylene, e.g., p-xylene, in the presence of a catalytic amount of trifluoromethanesulfonic acid while removing the water of reaction as a xylene-water azeotrope. Normally, this embodiment is carried out at a temperature of about 135° to 145° C. using about 25 to 50 mole percent trifluoromethanesulfonic acid per mole of aromatic acid.

My novel process is further illustrated by the following examples.

EXAMPLE 1

A mixture of p-toluic acid (22.2 g, 0.163 mole), p-xylene (100 mL), and trifluoromethanesulfonic acid (5 mL; 0.056 mole) was heated at reflux for 21 hours in a 300 mL flask equipped with a Dean-Stark trap, after which time 3 mL of water had been collected in the trap. The progress of the reaction was measured by gas chromatography as well as by the amount of water collected. After 6 hours, 22% of starting material had been converted to 2,5,4'-trimethylbenzophenone. The mixture was extracted with water, with 5% aqueous sodium hydroxide solution, and again with water. Evaporation of the organic layer gave 24 g (0.11 mole) of 2,5,4'-trimethylbenzophenone, 66% of theory.

COMPARATIVE EXAMPLE 1

The procedure of Example 1 was repeated except the Dean-Stark trap was not used and the water of reaction was not collected. After 4 hours of reflux, only about 6% of starting material had been converted to product (2,5,4'-trimethylbenzophenone). The amount of product was not increased significantly after refluxing an additional 6 hours.

EXAMPLE 2

Benzoic acid (20 g, 0.16 mole), p-xylene (100 mL), and trifluoromethanesulfonic acid (5 mL) were heated at reflux in a 300 mL flask equipped with a Dean-Stark trap. After 16 hours, the mixture was extracted with 100 mL of 6% aqueous sodium hydroxide, washed with water, dried over magnesium sulfate and evaporated to give 15.4 g (0.073 mole) of 2,5-dimethylbenzophenone. The aqueous sodium hydroxide extract was acidified to give 8.1 g (0.066 mole) of unreacted benzoic acid.

EXAMPLE 3

Hydroquinone (11.0 g, 0.1 mole), octanoic acid (30.2 g, 0.21 mole), heptane (110 mL), and methanesulfonic acid (10 mL, 0.14 mole) were heated at reflux (98° C.) for 5 hours in a 300 mL flask equipped with a Dean-Stark trap. During this time, 3 mL of water was collected. The sulfonic acid layer was separated, and the heptane layer was washed once with 50 mL of water and twice with 50 mL portions of saturated, aqueous sodium bicarbonate solution. The mixture was filtered to remove 5 g of product, octanoylhydroquinone octanoate ester, while evaporation of the organic layer gave 17.3 g. The total yield of octanoylhydroquinone was 22.3 g, 94% of theory.

The invention has been described in detail with particular reference to preferred embodiments thereof, but it will be understood that variations and modifications may be effected within the spirit and scope of the invention.

I claim:

1. Process for the preparation of an aryl ketone having the formula

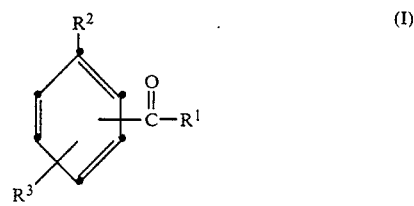

which comprises heating an aromatic compound having the formula

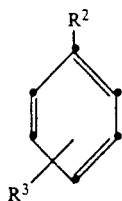 (II)

with a carboxylic acid in the presence of (1) a volatile, organic compound which forms an azeotrope with water and (2) a catalytic amount of an organic, sulfonic acid, whereby the water of reaction is removed as an azeotrope from the reaction mixture; wherein $R^1$ is the residue of said carboxylic acid;

$R^2$ individually is an alkyl, hydroxy, alkoxy alkanoyloxy or aryl radical;

$R^3$ is individually is hydrogen or one of the substituents which $R^2$ may represent; and $R^2$ and $R^3$ collectively represent a divalent chain of atoms forming a fused ring with the benzene ring to which each is attached.

2. Process according to claim 1 the process is carried out at a temperature of about 80° to 200° C.

3. Process according to claim 1 wherein the volatile, organic compound is selected from aliphatic and aromatic hydrocarbons.

4. Process for the preparation of a compound having the formula

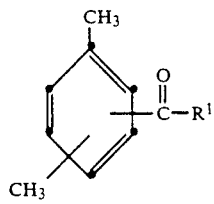

which comprises heating an aromatic compound having the formula

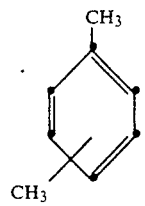 (II)

with benzoic or toluic acid in the presence of a catalytic amount of trifluoromethanesulfonic acid, whereby the water of reaction is removed as an azeotrope from the reaction mixture, wherein $R^1$ is phenyl or tolyl.

5. Process for the preparation of a compound having the formula

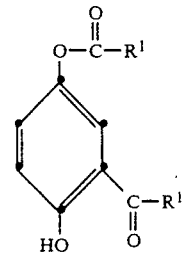

which comprises heating hydroquinone with a carboxylic acid having the formula

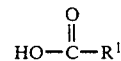

in the presence of (1) a volatile, organic compound which forms an azeotrope with water, and (2) a catalytic amount of an organic, sulfonic acid, whereby the water of reaction is removed as an azeotrope from the reaction mixture, wherein $R^1$ is alkyl of up to 19 carbon atoms.

* * * * *